(12) United States Patent
Lee et al.

(10) Patent No.: US 8,852,898 B2
(45) Date of Patent: Oct. 7, 2014

(54) L-THREONINE OVERPRODUCING MICROORGANISM AND METHOD FOR PREPARING L-THREONINE USING THE SAME

(75) Inventors: Sang Yup Lee, Daejeon (KR); Kwang Ho Lee, Daejeon (KR); Jin Hwan Park, Daejeon (KR); Tae Yong Kim, Daejeon (KR)

(73) Assignee: Korea Advanced Institute of Science & Technology, Yuseong-gu, Daejeon (KR)

( * ) Notice: Subject to any disclaimer, the term of this patent is extended or adjusted under 35 U.S.C. 154(b) by 1500 days.

(21) Appl. No.: 12/160,126

(22) PCT Filed: Jul. 2, 2007

(86) PCT No.: PCT/KR2007/003200
§ 371 (c)(1),
(2), (4) Date: Jul. 7, 2008

(87) PCT Pub. No.: WO2008/111708
PCT Pub. Date: Sep. 18, 2008

(65) Prior Publication Data
US 2011/0003349 A1 Jan. 6, 2011

(30) Foreign Application Priority Data

Mar. 9, 2007 (KR) .......................... 10-2007-0023370
Apr. 24, 2007 (KR) .......................... 10-2007-0039971

(51) Int. Cl.
C12P 13/08 (2006.01)
(52) U.S. Cl.
CPC ..................................... *C12P 13/08* (2013.01)
USPC .............. 435/115; 435/7.1; 435/320.1; 435/6

(58) Field of Classification Search
None
See application file for complete search history.

(56) References Cited

U.S. PATENT DOCUMENTS

| 6,083,752 A | 7/2000 | Ikenaka et al. ................ 435/440 |
| 2007/0025981 A1* | 2/2007 | Szalay et al. ............... 424/130.1 |

FOREIGN PATENT DOCUMENTS

| KR | 1020020096232 A | 12/2002 |
| KR | 1020050079338 A | 8/2005 |
| WO | WO2006/062327 A1 | 6/2006 |

OTHER PUBLICATIONS

Datsenko et al. (PNAS, 2000, vol. 97, No. 12, pp. 6440-6645).*
Datsenko and Wanner, "One-step Inactivation of Chromosomal Genes in *Escherichia coli* K-12 Using PCR Products," PNAS 2000 97(12):6640-6645.
Elisakova et al., "Feedback-Resistant Acetohydroxy Acid Synthase Increases Valine Production in *Corynebacterium glutamicum*," Appl. Environ. Microbiol. 2005:207-213.
Hayashi et al., "A *leuC* Mutation Leading to Increased L-Lysine Production and *rel*-Independent Global Expression Changes in *Corynebacterium glutamicum*," Appl. Microbiol. Biotechnol. 2006 (72):783-789.
Ohnishi et al., "A Novel Methodology Employing *Corynebacterium glutamicum* Genome Information to Generate a New L-Lysine-producing Mutant," Appl. Microbiol. Biotechnol. 2002 (58):217-223.
Peters-Wendisch et al., "Metabolic Engineering of *Corynebacterium glutamicum* for L-Serine Production," Appl. Environ. Microbiol. 2005:7139-7144.
Suzuki et al., "New Multiple-Deletion Method for the *Corynebacterium glutamicum* Genome, Using a Mutant *lox* Sequence," Appl. Environ. Microbiol. 2005:8472-8480.

* cited by examiner

*Primary Examiner* — Hope Robinson
(74) *Attorney, Agent, or Firm* — Licata & Tyrrell P.C.

(57) ABSTRACT

The present invention relates to a mutant microorganism producing a high concentration of L-threonine in high yield, prepared using site-specific mutation, not random mutation, such as treatment with a mutation inducer, a method for preparing the same, and a method for preparing L-threonine using the mutant microorganism producing L-threonine. By using the mutant microorganism according to the present invention, L-threonine can be prepared at high yield, additional strain development becomes possible and their physiological phenomena can be easily understood since genetic information of L-threonine producing microorganism can be identified.

3 Claims, 6 Drawing Sheets

SEQUENCE LISTING

<160> NUMBER OF SEQ ID NOS: 58

<210> SEQ ID NO 1
<211> LENGTH: 66
<212> TYPE: DNA
<213> ORGANISM: Artificial Sequence
<220> FEATURE:
<223> OTHER INFORMATION: primer

<400> SEQUENCE: 1
agccgtcgac gctagcgcat gcacgcgtgt gcacccatgg gacgtcctca ctgactcgct        60
gcgctc                                                                  66

<210> SEQ ID NO 2
<211> LENGTH: 57
<212> TYPE: DNA
<213> ORGANISM: Artificial Sequence
<220> FEATURE:
<223> OTHER INFORMATION: primer

<400> SEQUENCE: 2
ggctcacaac gtggctagcg acgtcgtgca cccatgggtt ccactgagcg tcagacc          57

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
actctctaga cgcgggtttg ttactgataa                                         30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
gctagatatc aggatatcgg cattttcttt                                         30

<210> SEQ ID NO 5
<211> LENGTH: 72
<212> TYPE: DNA
<213> ORGANISM: Artificial Sequence
<220> FEATURE:
<223> OTHER INFORMATION: primer

<400> SEQUENCE: 5
gtgaaaccag taacgttata cgatgtcgca gagtatgccg gtgtctctta gattgcagca        60
ttacacgtct tg                                                            72

<210> SEQ ID NO 6
<211> LENGTH: 70
<212> TYPE: DNA
<213> ORGANISM: Artificial Sequence
<220> FEATURE:
<223> OTHER INFORMATION: primer

<400> SEQUENCE: 6
tcactgcccg ctttccagtc gggaaacctg tcgtgccagc tgcattaatg cacttaacgg        60
ctgacatggg                                                               70

```
<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
acgcggatcc atcgccatta tggccggcgt attagaagc                    39

<210> SEQ ID NO 8
<211> LENGTH: 43
<212> TYPE: DNA
<213> ORGANISM: Artificial Sequence
<220> FEATURE:
<223> OTHER INFORMATION: primer

<400> SEQUENCE: 8
gattgcgtaa tcagcaccac gaaaatacgg gcgcgtgaca tcg               43

<210> SEQ ID NO 9
<211> LENGTH: 43
<212> TYPE: DNA
<213> ORGANISM: Artificial Sequence
<220> FEATURE:
<223> OTHER INFORMATION: primer

<400> SEQUENCE: 9
cgatgtcacg cgcccgtatt ttcgtggtgc tgattacgca atc               43

<210> SEQ ID NO 10
<211> LENGTH: 38
<212> TYPE: DNA
<213> ORGANISM: Artificial Sequence
<220> FEATURE:
<223> OTHER INFORMATION: primer

<400> SEQUENCE: 10
cacgcgtcga cctggaagtg cagttaacaa tgaccggg                     38

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
ctgatgtcga ccctgctgtt tgttgagatc ctgcgc                       36

<210> SEQ ID NO 12
<211> LENGTH: 43
<212> TYPE: DNA
<213> ORGANISM: Artificial Sequence
<220> FEATURE:
<223> OTHER INFORMATION: primer

<400> SEQUENCE: 12
ggttgaaccg gtggtatcaa ggataatgcc acgctcactt ctg               43

<210> SEQ ID NO 13
<211> LENGTH: 44
<212> TYPE: DNA
<213> ORGANISM: Artificial Sequence
<220> FEATURE:
```

<223> OTHER INFORMATION: primer

<400> SEQUENCE: 13
cagaagtgag cgtggcatta atccttgata ccaccggttc aacc            44

<210> SEQ ID NO 14
<211> LENGTH: 35
<212> TYPE: DNA
<213> ORGANISM: Artificial Sequence
<220> FEATURE:
<223> OTHER INFORMATION: primer

<400> SEQUENCE: 14
ccagctaaat gacgcttcag gatccggttt ataag                      35

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15
gcagccagct gtagcgatct gcggattgtc gatagt                     36

<210> SEQ ID NO 16
<211> LENGTH: 36
<212> TYPE: DNA
<213> ORGANISM: Artificial Sequence
<220> FEATURE:
<223> OTHER INFORMATION: primer

<400> SEQUENCE: 16
caggagcatg ccagaagctg ctatcagaca ctcttt                     36

<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
cagcagaatt catgcgagtg ttgaagttcg gcggta                     36

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
cagagctgca gtccgtccaa atctcgcaac aatcgg                     36

<210> SEQ ID NO 19
<211> LENGTH: 72
<212> TYPE: DNA
<213> ORGANISM: Artificial Sequence
<220> FEATURE:
<223> OTHER INFORMATION: primer

<400> SEQUENCE: 19
atgccacatt cactgttcag caccgatacc gatctcaccg ccgaaaatct gattgcagca   60
ttacacgtct tg                                               72

<210> SEQ ID NO 20
<211> LENGTH: 71
<212> TYPE: DNA
<213> ORGANISM: Artificial Sequence
<220> FEATURE:
<223> OTHER INFORMATION: primer

<400> SEQUENCE: 20
gttgataagg aacagaaagc ccaccgcccg cagaaatagc ctgtaaatcc cacttaacgg    60
ctgacatggg a                                                         71

<210> SEQ ID NO 21
<211> LENGTH: 77
<212> TYPE: DNA
<213> ORGANISM: Artificial Sequence
<220> FEATURE:
<223> OTHER INFORMATION: primer

<400> SEQUENCE: 21
gtgtgccgga cgagctaccc gccgtcaatt tcttgcgtga agaaaacgtc tttgtgattg    60
cagcattaca cgtcttg                                                   77

<210> SEQ ID NO 22
<211> LENGTH: 71
<212> TYPE: DNA
<213> ORGANISM: Artificial Sequence
<220> FEATURE:
<223> OTHER INFORMATION: primer

<400> SEQUENCE: 22
cgggatggcc cgtcacaaag gcaatgcgct tatctttact ggcaaacaga cacttaacgg    60
ctgacatggg a                                                         71

<210> SEQ ID NO 23
<211> LENGTH: 72
<212> TYPE: DNA
<213> ORGANISM: Artificial Sequence
<220> FEATURE:
<223> OTHER INFORMATION: primer

<400> SEQUENCE: 23
atgaaagcgt tatccaaact gaaagcggaa gagggcatct ggatgaccga gattgcagca    60
ttacacgtct tg                                                        72

<210> SEQ ID NO 24
<211> LENGTH: 71
<212> TYPE: DNA
<213> ORGANISM: Artificial Sequence
<220> FEATURE:
<223> OTHER INFORMATION: primer

<400> SEQUENCE: 24
atcactttgg tccagtcgat agacatatca gacggcggaa tacccagcat cacttaacgg    60
ctgacatggg a                                                         71

<210> SEQ ID NO 25
<211> LENGTH: 72
<212> TYPE: DNA
<213> ORGANISM: Artificial Sequence
<220> FEATURE:
<223> OTHER INFORMATION: primer

<400> SEQUENCE: 25
tgaaaatgat tccacgata cagaaaaaag agactgtcat ggtcgcaccc gattgcagca    60
ttacacgtct tg    72

<210> SEQ ID NO 26
<211> LENGTH: 71
<212> TYPE: DNA
<213> ORGANISM: Artificial Sequence
<220> FEATURE:
<223> OTHER INFORMATION: primer

<400> SEQUENCE: 26
atagaaattg cggcaaacgg ttcacggtgc tcatcgaaaa tacacgctgc cacttaacgg    60
ctgacatggg a    71

<210> SEQ ID NO 27
<211> LENGTH: 72
<212> TYPE: DNA
<213> ORGANISM: Artificial Sequence
<220> FEATURE:
<223> OTHER INFORMATION: primer

<400> SEQUENCE: 27
atcgccagcc agtgcacagc tttaagctgc gcggcgcata cgccatgatg gattgcagca    60
ttacacgtct tg    72

<210> SEQ ID NO 28
<211> LENGTH: 71
<212> TYPE: DNA
<213> ORGANISM: Artificial Sequence
<220> FEATURE:
<223> OTHER INFORMATION: primer

<400> SEQUENCE: 28
cccctgctgc tgtgacagtt cgatcgcttt ggctttcgct tcatcaaagt cacttaacgg    60
ctgacatggg a    71

<210> SEQ ID NO 29
<211> LENGTH: 38
<212> TYPE: DNA
<213> ORGANISM: Artificial Sequence
<220> FEATURE:
<223> OTHER INFORMATION: primer

<400> SEQUENCE: 29
gacgggatcc gcaaagcctg tgcgctgatc accgacgg    38

<210> SEQ ID NO 30
<211> LENGTH: 38
<212> TYPE: DNA
<213> ORGANISM: Artificial Sequence
<220> FEATURE:
<223> OTHER INFORMATION: primer

<400> SEQUENCE: 30
cacgcctaac cgcgcagaaa aaaacgcgac gccctgcg    38

<210> SEQ ID NO 31
<211> LENGTH: 38
<212> TYPE: DNA
<213> ORGANISM: Artificial Sequence
<220> FEATURE:
<223> OTHER INFORMATION: primer

<400> SEQUENCE: 31
cgcagggcgt cgcgttttt tctgcgcggt taggcgtg                                    38

<210> SEQ ID NO 32
<211> LENGTH: 40
<212> TYPE: DNA
<213> ORGANISM: Artificial Sequence
<220> FEATURE:
<223> OTHER INFORMATION: primer

<400> SEQUENCE: 32
caggtactgc agaccggaaa gaatatgcgc cagccgttcg                                 40

<210> SEQ ID NO 33
<211> LENGTH: 64
<212> TYPE: DNA
<213> ORGANISM: Artificial Sequence
<220> FEATURE:
<223> OTHER INFORMATION: primer

<400> SEQUENCE: 33
atataagctt taccgttcgt atagcataca ttatacgaag ttatctgccc tgaaccgacg           60
accg                                                                       64

<210> SEQ ID NO 34
<211> LENGTH: 65
<212> TYPE: DNA
<213> ORGANISM: Artificial Sequence
<220> FEATURE:
<223> OTHER INFORMATION: primer

<400> SEQUENCE: 34
aattcccggg taccgttcgt ataatgtatg ctatacgaag ttatgcatca cccgacgcac           60
tttgc                                                                      65

<210> SEQ ID NO 35
<211> LENGTH: 71
<212> TYPE: DNA
<213> ORGANISM: Artificial Sequence
<220> FEATURE:
<223> OTHER INFORMATION: primer

<400> SEQUENCE: 35
ctgcgggcaa ccatgcgcaa ggggtttccc tctcctgcgc gatgctgggt taggtgacac           60
tatagaacgc g                                                               71

<210> SEQ ID NO 36
<211> LENGTH: 66
<212> TYPE: DNA
<213> ORGANISM: Artificial Sequence
<220> FEATURE:
<223> OTHER INFORMATION: primer

<400> SEQUENCE: 36
ggcagctaaa ggcaaagaac atcaccactg caaccatcag catgcttagt ggatctgatg           60
ggtacc                                                                     66

<210> SEQ ID NO 37
<211> LENGTH: 70
<212> TYPE: DNA
<213> ORGANISM: Artificial Sequence
<220> FEATURE:

<223> OTHER INFORMATION: primer

<400> SEQUENCE: 37

| attaagttca ctgaccgatg cggaaaaacg caaaggcgtg gtggcctgtt ctgcgggcaa | 60 |
| ccatgcgcaa | 70 |

<210> SEQ ID NO 38
<211> LENGTH: 65
<212> TYPE: DNA
<213> ORGANISM: Artificial Sequence
<220> FEATURE:
<223> OTHER INFORMATION: primer

<400> SEQUENCE: 38

| tctgcgcttt ggcttccgcc atgttggccg gagacagagt aaacaggcag ctaaaggcaa | 60 |
| agaac | 65 |

<210> SEQ ID NO 39
<211> LENGTH: 71
<212> TYPE: DNA
<213> ORGANISM: Artificial Sequence
<220> FEATURE:
<223> OTHER INFORMATION: primer

<400> SEQUENCE: 39

| ctgcgggcaa ccatgcgcaa ggggtttccc tctcctgcgc gatgctgggt taggtgacac | 60 |
| tatagaacgc g | 71 |

<210> SEQ ID NO 40
<211> LENGTH: 65
<212> TYPE: DNA
<213> ORGANISM: Artificial Sequence
<220> FEATURE:
<223> OTHER INFORMATION: primer

<400> SEQUENCE: 40

| tctgcgcttt ggcttccgcc atgttggccg gagacagagt aaacaggcag ctaaaggcaa | 60 |
| agaac | 65 |

<210> SEQ ID NO 41
<211> LENGTH: 70
<212> TYPE: DNA
<213> ORGANISM: Artificial Sequence
<220> FEATURE:
<223> OTHER INFORMATION: primer

<400> SEQUENCE: 41

| attaagttca ctgaccgatg cggaaaaacg caaaggcgtg gtggcctgtt ctgcgggcaa | 60 |
| ccatgcgcaa | 70 |

<210> SEQ ID NO 42
<211> LENGTH: 71
<212> TYPE: DNA
<213> ORGANISM: Artificial Sequence
<220> FEATURE:
<223> OTHER INFORMATION: primer

<400> SEQUENCE: 42

| ctgcgggcaa ccatgcgcaa ggggtttccc tctcctgcgc gatgctgggt taggtgacac | 60 |
| tatagaacgc g | 71 |

<210> SEQ ID NO 43
<211> LENGTH: 66
<212> TYPE: DNA
<213> ORGANISM: Artificial Sequence
<220> FEATURE:
<223> OTHER INFORMATION: primer

<400> SEQUENCE: 43
ggcagctaaa ggcaaagaac atcaccactg caaccatcag catgcttagt ggatctgatg      60
ggtacc                                                                66

<210> SEQ ID NO 44
<211> LENGTH: 70
<212> TYPE: DNA
<213> ORGANISM: Artificial Sequence
<220> FEATURE:
<223> OTHER INFORMATION: primer

<400> SEQUENCE: 44
attaagttca ctgaccgatg cggaaaaacg caaaggcgtg gtggcctgtt ctgcgggcaa      60
ccatgcgcaa                                                            70

<210> SEQ ID NO 45
<211> LENGTH: 61
<212> TYPE: DNA
<213> ORGANISM: Artificial Sequence
<220> FEATURE:
<223> OTHER INFORMATION: primer

<400> SEQUENCE: 45
gcccctatgt gtaacaaata accacactgt gaatgttgtc taggtgacac tatagaacgc      60
g                                                                     61

<210> SEQ ID NO 46
<211> LENGTH: 77
<212> TYPE: DNA
<213> ORGANISM: Artificial Sequence
<220> FEATURE:
<223> OTHER INFORMATION: primer

<400> SEQUENCE: 46
tgttatccgc tcacaattcc acacattata cgagccggat gattaattgt caacagctag      60
tggatctgat gggtacc                                                    77

<210> SEQ ID NO 47
<211> LENGTH: 60
<212> TYPE: DNA
<213> ORGANISM: Artificial Sequence
<220> FEATURE:
<223> OTHER INFORMATION: primer

<400> SEQUENCE: 47
tcacgacagt aaccgcacct acactgtcat gacattgctc gcccctatgt gtaacaaata      60

<210> SEQ ID NO 48
<211> LENGTH: 81
<212> TYPE: DNA
<213> ORGANISM: Artificial Sequence
<220> FEATURE:
<223> OTHER INFORMATION: primer

<400> SEQUENCE: 48
cgatgttggc aggaatggtg tgtttgtgaa tttggctcat ggtctgtttc ctgtgtgaaa      60
ttgttatccg ctcacaattc c                                              81

<210> SEQ ID NO 49
<211> LENGTH: 60
<212> TYPE: DNA
<213> ORGANISM: Artificial Sequence
<220> FEATURE:
<223> OTHER INFORMATION: Primer

<400> SEQUENCE: 49
cgaattgcgc cattgttgca atggcggttt ttattgtttt tcacgacagt aaccgcacct    60

<210> SEQ ID NO 50
<211> LENGTH: 70
<212> TYPE: DNA
<213> ORGANISM: Artificial Sequence
<220> FEATURE:
<223> OTHER INFORMATION: Primer

<400> SEQUENCE: 50
ttgttgatac atcgcctcgt actgctgagg gtttatcagg caacggtctg cgatgttggc    60
aggaatggtg                                                           70

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
gttgcccggg atgcgagtgt tgaagttcgg                                     30

<210> SEQ ID NO 52
<211> LENGTH: 31
<212> TYPE: DNA
<213> ORGANISM: Artificial Sequence
<220> FEATURE:
<223> OTHER INFORMATION: primer

<400> SEQUENCE: 52
gcgtcaagct tcggcggttg ttattctccg c                                   31

<210> SEQ ID NO 53
<211> LENGTH: 34
<212> TYPE: DNA
<213> ORGANISM: Artificial Sequence
<220> FEATURE:
<223> OTHER INFORMATION: primer

<400> SEQUENCE: 53
ctgagaattc ggatccagat ggctgaacag atgc                                34

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
cctacaagct tagatctcaa agcagatgaa ggcgc                               35

<210> SEQ ID NO 55
<211> LENGTH: 29

```
<212> TYPE: DNA
<213> ORGANISM: Artificial Sequence
<220> FEATURE:
<223> OTHER INFORMATION: primer

<400> SEQUENCE: 55
ctgaacgcgt gaactgcgta agtattacg                                     29

<210> SEQ ID NO 56
<211> LENGTH: 36
<212> TYPE: DNA
<213> ORGANISM: Artificial Sequence
<220> FEATURE:
<223> OTHER INFORMATION: primer

<400> SEQUENCE: 56
ctgacgtcga cctgcagacc atgcagaaat gtaaat                             36

<210> SEQ ID NO 57
<211> LENGTH: 30
<212> TYPE: DNA
<213> ORGANISM: Artificial Sequence
<220> FEATURE:
<223> OTHER INFORMATION: primer

<400> SEQUENCE: 57
cgtagctgca gtccacacca gtaaactctg                                    30

<210> SEQ ID NO 58
<211> LENGTH: 36
<212> TYPE: DNA
<213> ORGANISM: Artificial Sequence
<220> FEATURE:
<223> OTHER INFORMATION: primer

<400> SEQUENCE: 58
catttcggcc ggacgtcagt cggataaggc gtttac                             36
```

L-THREONINE OVERPRODUCING MICROORGANISM AND METHOD FOR PREPARING L-THREONINE USING THE SAME

This patent application is the National Stage of International Application No. PCT/KR2007/003200 filed Jul. 2, 2007, which claims the benefit of priority from Korean Application No. 10-2007-0039971, filed Apr. 24, 2007, and Korean Application No. 10-2007-0023370, filed Mar. 9, 2007 each of which are herein incorporated by reference in their entirety.

TECHNICAL FIELD

The present invention relates to a mutant microorganism producing L-threonine in high yield and a method for preparing L-threonine using the same, and more specifically, relates to a mutant microorganism producing a high concentration of L-threonine in high yield which is prepared by site-specific mutation, not random mutation, such as treatment with a mutation inducer, a method for preparing the mutant microorganism producing a high concentration of L-threonine in high yield, and a method for preparing L-threonine using the same.

BACKGROUND ART

L-threonine has been produced by microorganism fermentation, and it has been prepared using mutant strains induced through screening process by treating, with a mutation inducer, wild type strains of microorganism belonging to the genus *Escherichia, Corynebacterium, Brevibacterium*, and *Serratia*. For example, Korean Patent 115393 describes a method for screening microorganisms producing L-threonine by treating a microorganism belonging to the genus *Escherichia* with N-methyl-N'-nitro-N-nitrosoguanidine, which is a kind of random mutation inducer, to give tolerance to purine analogs, such as 6-dimethylaminopurine, 9-azaadenine, and 8-azadiaminopurine, etc. Korean Patent 168719 describes a method for screening microorganisms producing L-threonine from wild type strain of *Serratia* sp. through rendering tolerance to lysine analog S-(2-aminoethyl)-L-cysteine, and rifampicin, an antibiotic using a mutation inducer. Moreover, Japanese Patent Publication 224684/83 describes a method of using a microorganism which belongs to *Brevibacterium* sp., has tolerance to S-(2-aminoethyl)-L-cystein and α-amino-β-hydroxyvalerate, and has a nutritional requirement for L-isoleucine and L-lysine.

Meanwhile, technologies for developing more improved L-threonine-producing microorganisms by introducing site-specific gene substitution, gene amplification and distruction, etc., into L-threonine-producing microorganisms developed by random mutation as gene recombinantion technology develops, are being reported. For example, Korean Patent 397423 describes a method for preparing L-threonine using a microorganism in which at least one copy of phosphoenolpyruvic acid carboxylase (ppc) gene and threonine operon are inserted into a specific site in a chromosomal DNA of L-threonine-producing microorganisms prepared by repetitive mutation induction and screening process to have methionine requirement, tolerance to threonine analogus (α-amino-β-hydroxyvalerate), tolerance to lysine analogus (S-(2-aminoethyl)-L-cystein), and tolerance to isoleucine analogus (e.g., α-aminobutyric acid), using genetic engineering techniques. In addition to that, many technologies for the development of L-threonine-producing microorganisms by applying gene recombination to a mutant microorganism as described above, have been also reported (US 2005/0032178, US 2004/0214294, U.S. Pat. No. 5,939,307).

However, the above-described methods have several critical disadvantages as they were developed on the basis of microorganisms prepared by treating them with a mutation inducer inducing random mutation. Treatment with a mutation inducer and microorganism screening enabled the development a strain capable of producing L-threonine in high yield, but screened microorganisms have various physiological characteristics, such as a decline in the growth rate of a strain compared to its parent strain, a decline in sugar consumption rate, and a decline in tolerance to external environmental change, which is disadvantageous for industrial production of amino acids due to many random mutations inevitably resulted from the treatment with a mutation inducer. Moreover, they have disadvantages in that there are many problems in additional strain development due to many mutants produced by treatment with a mutation inducer and there is a limitation in improving their productivity.

Accordingly, as total chromosome sequences of microorganisms were identified due to the development of genetic engineering, recently, new attempts, excluding random mutation, to overcome the above mentioned problems of random mutation have been made. A study on the development of a strain producing lysine in high yield by screening major mutants advantageous for producing lysine using comparative genomics study between lysine-producing *Corynebacterium* sp. developed by repetitive random mutation and a wild type strain of *Corynebacterium* sp., has been reported (Ohnishi, J. et al., *Appl. Microbiol. Biotechnol.*, 58:217, 2003; Hayashi, M. et al., *Appl. Microbiol. Biotechnol.*, 72:783, 2006).

Moreover, Veronika et al. reported that after ilvA and panB were inactivated using *Corynebacterium* sp., and operon (ilvBNC) involved in L-valine biosynthesis was amplified, 130 mM L-valine was produced by disrupting feedback inhibition in ilvN gene (Veronika et al., *Appl. Environ. Microbiol.*, 71:207, 2005). Also, it was reported that 86 mM L-serine was produced by rational design using *Corynebacterium* sp. (Peters-Wendisch et al., *Appl. Environ. Microbiol.*, 71:7139, 2005). All of the reports are study results on strain development obtained by carrying out only site-specific mutation by rational design excluding random mutation, but they have very poor industrial applicability except for the above mentioned lysine-producing microorganism. Moreover, it has not yet been reported that L-threonine was produced at high yield by strain development using rational design.

Therefore, there is an urgent need to develop a strain producing L-threonine in high yield by ration design methods, which can overcome the disadvantages of strain development by the existing random mutation method.

Accordingly, the present inventors have made extensive efforts to develop a mutant microorganism which can overcome disadvantages of microorganisms prepared by the existing random mutation method, and as a result, constructed a mutant microorganism producing L-threonine using only site-specific mutation, and confirmed that a high concentration of L-theronine can be produced at high yield using the mutant microorganism, thereby completing the present invention.

SUMMARY OF THE INVENTION

Therefore, the main object of the present invention is to provide a method for preparing a mutant microorganism producing a high concentration of L-threonine in high yield, the method comprising using only site-specific mutation.

Another object of the present invention is to provide a mutant microorganism producing a high concentration of L-threonine in high yield, which is constructed using the above-described method, and a method for producing L-threonine, which comprises culturing the microorganism, and recovering L-threonine from culture broth.

To achieve the above objects, the present invention provides a method for preparing a mutant microorganism producing a high concentration of L-threonine in high yield, using site-specific mutation, the method comprising (a) disrupting a gene encoding repressor of lac operon, a gene encoding homoserine O-succinyltransferase, a gene encoding diaminopimelate decarboxylase and a gene encoding L-threonine dehydrogenase; (b) mutating a gene encoding aspartokinase I and aspartokinase III to prevent the inhibition of aspartokinase I and aspartokinase III activities; and (c) inducing the substitution of a promoter of L-threonine operon or acetyl CoA synthetase with a strong promoter.

The present invention also provides a method for preparing a recombinant mutant microorganism, which comprises introducing a vector containing one or more genes selected from the group consisting of a gene encoding L-theronine operon, a gene encoding a threonine exporter, a gene encoding theronine and homoserine exporter, and a gene encoding homoserine and homoserine lactone exporter, into the mutant microorganism prepared by the above-described method.

The present invention also provides a mutant microorganism producing a high concentration of L-threonine in high yield, in which (a) a gene encoding repressor of lac operon, a gene encoding homoserine O-succinyltransferase, a gene encoding diaminopimelate decarboxylase and a gene encoding L-threonine dehydrogenase are disrupted, (b) a gene encoding aspartokinase I and aspartokinase III is mutated to prevent the inhibition of aspartokinase I and aspartokinase III activities, and (c) a strong promoter is substituted for a promoter of L-threonine operon or acetyl CoA synthetase.

The present invention also provides a recombinant mutant microorganism, which has a vector containing one or more genes selected from the group consisting of a gene encoding L-theronine operon, a gene encoding a threonine exporter, a gene encoding theronine and homoserine exporter, and a gene encoding homoserine-homoserine lactone exporter, introduced thereinto.

The present invention also provides a vector for one-step inactivation, which contains lox66 gene, lox71 gene and an antibiotic resistance marker gene.

The present invention also provides a method for producing L-threonine, the method comprises culturing the microorganism, and recovering L-threonine from culture broth.

Other features and embodiments of the present invention will be more fully apparent from the following detailed description and appended claims.

DETAILED DESCRIPTION OF THE INVENTION, AND PREFERRED EMBODIMENTS

Figure 1:
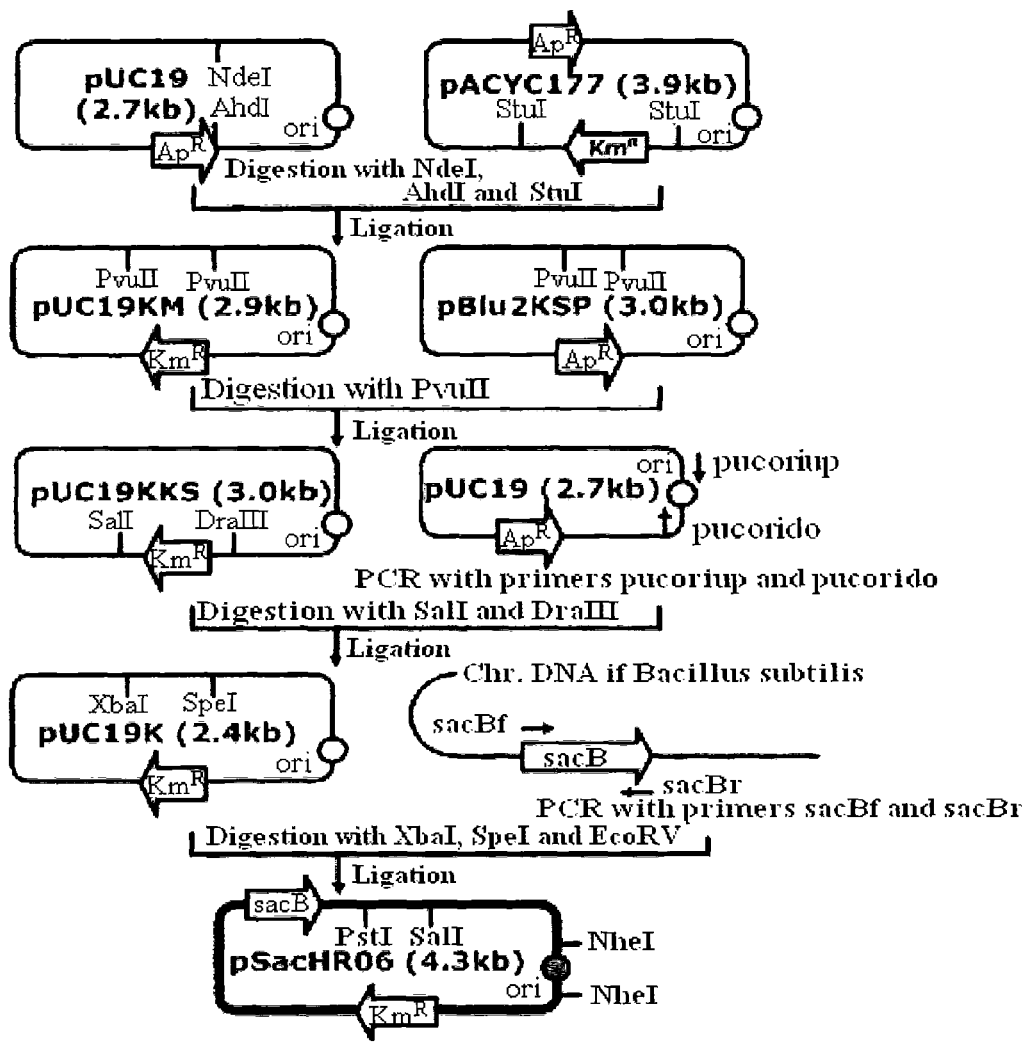
FIG. 1 shows a process for constructing pSacHR06 vector.

In one aspect, the present invention relates to a method for preparing a mutant microorganism producing a high concentration of L-threonine in high yield using site-specific mutation, the method comprises: (a) disrupting a gene encoding repressor of lac operon, a gene encoding homoserine O-succinyltransferase, a gene encoding diaminopimelate decarboxylase and a gene encoding L-threonine dehydrogenase; (b) mutating a gene encoding aspartokinase I and aspartokinase III to prevent the inhibition of aspartokinase I and aspartokinase III activities; and (c) inducing the substitution of a promoter of L-threonine operon or acetyl CoA synthetase with a strong promoter.

In the method for preparing a mutant microorganism according to the present invention, in case of disrupting a gene encoding a regulatory protein which inhibits the expression of glyoxylate shunt, and a gene encoding threonine/serine transporter, L-threonine productivity can be increased. In addition, in case of substituting a promoter of a gene encoding phosphoenolpyruvate carboxylase with a strong promoter, L-threonine productivity can be increased.

In another aspect, the present invention relates to a method for preparing a recombinant mutant microorganism, the method comprises introducing a vector containing one or more genes selected from the group consisting of a gene encoding L-theronine operon, a gene encoding a threonine exporter, a gene encoding theronine and homoserine exporter, and a gene encoding homoserine-homoserine lactone exporter, into the mutant microorganism prepared using the above-described method.

In still another aspect, the present invention relates to a mutant microorganism producing a high concentration of L-threonine in high yield, in which (a) a gene encoding repressor of lac operon, a gene encoding homoserine O-succinyltransferase, a gene encoding diaminopimelate decarboxylase and a gene encoding L-threonine dehydrogenase are disrupted, (b) a gene encoding aspartokinase I and aspartokinase III is mutated to prevent the inhibition of aspartokinase I and aspartokinase III activities, and (c) a strong promoter is substituted for a promoter of L-threonine operon or acetyl CoA synthetase.

In the present invention, the microorganism is selected from the group consisting of bacteria, yeast and fungi, and the bacteria is selected from the group consisting of Corynebacteium sp., Brevibacterium sp. and E. coli.

In the mutant microorganism according to the present invention, preferably, a gene encoding a regulatory protein which inhibits the expression of glyoxylate shunt and a gene encoding threonine/serine transporter are additionally disrupted, and a promoter of a gene encoding phosphoenolpyruvate carboxylase is additionally substituted with a strong promoter.

In the present invention, the strong promoter is selected from the group consisting of trc promoter, tac promoter, T7 promoter, lac promoter and trp promoter.

In another aspect, the present invention relates to a recombinant mutant microorganism, in which a vector containing one or more genes selected from the group consisting of a gene encoding L-theronine operon, a gene encoding a threonine exporter, a gene encoding theronine and homoserine exporter, and a gene encoding homoserine-homoserine lactone exporter, is introduced into the mutant microorganism.

In the present invention, both prokaryotic and eukaryotic microorganisms can be used without limitations as long as the parent strain of a mutant microorganism can produce L-threonine and the mutant microorganism does not have random mutation.

For example, it may include strains of microorganism belonging to the genus Escherichia, Erwinia, Serratia, Providencia, Corynebacterium and Brevibacterium, it may preferably be a microorganism belonging to the Enterobacteriaceae family, more preferably a microorganism belonging to the genus Escherichia.

Moreover, the mutation inducers of random mutation include all materials which are used in physical or chemical method known in the art. For example, the inducers used in physical method include all materials inducing random mutation including X-ray or UV-ray etc., and the materials used in chemical method include all chemical mutanting agents including N-methyl-N'-nitro-N-nitrosoguanidine (NTG), diethyl sulfate and ethylamine, etc.

In the mutant microorganism according to the present invention, preferably, feedback inhibition, which is a major regulatory mechanism involved in producing L-threonine, and attenuation are removed by site-specific mutation, lysine biosynthetic pathway, methionine biosynthetic pathway, and a decomposition pathway of threonine, etc., which is compete with L-threonine biosynthetic pathway, are inactivated, L-isoleucine biosynthesis pathway from L-threonine is weakened, and an operon promoter involved in L-threonine biosynthesis and a site containing an attenuator are substituted with a strong promoter.

In another embodiment of the present invention, the mutant microorganism preferably has iclR inactivated to increase the amount of oxaloacetate, a major precursor for L-threonine biosynthesis, and preferably has a bative promoter of ppc gene on chromosome substituted with a strong promoter. Moreover, the mutant microorganism preferably has an L-theronine thrABC operon and genes, such as rhtC, rhtA, and rhtB, etc., involved in eliminating L-threonine in cells, inserted into a recombinant vector to improve their activity.

In the present invention, the inactivation of lysine biosynthesis pathway is preferably by inactivating lysA (gene encoding diaminopimelate decarboxylase) which is a gene encoding an enzyme involved in L-lysine biosynthesis, the inactivation of methionine biosynthesis pathway is preferably by inactivating metA (gene encoding homoserine O-succinyltransferase) which is a gene encoding an enzyme involved in L-methionine biosynthesis, and the inactivation of a decomposition pathway of threonine is preferably by inactivating tdh (gene encoding L-threonine dehydrogenase) and tdcC (gene encoding threonine/serine transporter).

Moreover, weakening of L-isoleucine biosynthesis pathway is preferably caused by site-specifically mutating ilvA gene (gene encoding threonine dehydratase) to result in weak enzymatic activity thereof.

In the present invention, the inactivated gene refers to a polynucleotide sequence which contains a polynucleotide sequence having a sequence homolog to the corresponding gene in a host, but cannot express activated protein products due to introduction of mutation, such as destruction, substitution, truncation and inversion. Introduction of the inactivated gene or its fragment into host cells can be carried out by, for example, transformation, conjugation, transduction or electroporation, but it is not limited to these examples.

In another aspect, the present invention relates to a vector for one-step inactivation, which contains lox66 gene, lox71 gene and an antibiotic resistance marker gene. In the present invention, the vector is preferably pMloxC.

In another aspect, the present invention relates to a method for producing L-threonine, which comprises culturing the microorganism producing L-threonine in high yield, and recovering L-threonine from culture broth.

In the method for preparing L-threonine according to the present invention, the process of culturing the microorganism can be performed according to suitable culture media and culture conditions known in the art. The culturing process can be easily used by adjusting according to selected microorganism by a person skilled in the art. The examples of the culturing method include batch culture, continuos culture and fed-batch culture, but it is not limited thereto.

Moreover, isolation of L-threonine from the culture broth can be performed by a conventional method known in the art. The isolation method may include centrifugation, filtration, ion exchange chromatography and crystallization, etc. For example, a supernant, obtained by centrifuging culture broth at a low speed and removing biomass, can be isolated by ion exchange chromatography, but it is not limited to these examples.

EXAMPLES

Hereinafter, the present invention will be described in more detail by specific examples. However, the present invention is not limited to these examples, and it is obvious to those of ordinary skill in the field of the present invention that numerous variations or modifications could be made within the spirit and scope of the present invention.

The following examples illustrate that a microorganism producing a high concentration of L-threonine is prepared by introducing site-specific gene mutation into E coli W3110. However, it is obvious to a person skilled in the art that microorganisms producing a high concentration of L-threonine in high yield can be constructed by site-specifically disrupting and mutating the same gene as described above using other E coli and microorganisms.

Example 1

Construction of Microorganism Having a High Ability to Produce L-Threonine 1-1: Construction of pSacHR06

In order to disrupt feedback inhibition of thrA, pSacHR06 vector was constructed for the purpose of using homologous recombination of sacB origined from Bacillus subtilus (Wohlleben et al., J. Bacteriol., 174:5462, 1992) to substitute a specific base or bases of chromosome DNA (FIG. 1).

First, to substitute ampicillin resistance gene in pUC19 vector (New England Biolab, USA) with kanamycin resistance gene, pUC19KM vector was constructed by ligating 1.5 kb fragment obtained by cutting pUC19 with NdeI and AhdI, and 1.3 kb fragment obtained by cutting pACYC177 vector (New England Biolab, USA) with Stu I.

And then, pUC19KKS vector was constructed by ligating 2.5 kb fragment obtained by cutting pUC19KM vector with PvuII, and a 400 bp fragment obtained by cutting pBluescript II KS(+) vector with PvuII. To easily remove the origin of DNA replication of pUC19KKS vector, pUC19 vector, as a template, was subjected to PCR using primers set forth in SEQ ID NO: 1 and SEQ ID NO: 2 below. As a result, DNA fragment, which has recognition site of same restriction enzymes at both ends and the origin of DNA replication, was obtained. The obtained PCR fragment was cut with SacI and DraIII, and ligated with 1.5 kb fragment obtained by cutting pUC19KKS vector with SacI and DraIII, thereby constructing pUC19K vector. To introduce sacB gene from *Bacillus subtilus* into the pUC19K vector, the genomic DNA of *Bacillus subtilus*, as a template, was subjected to PCR using primers set forth in SEQ ID NO: 3 and SEQ ID NO: 4 below, and then, DNA fragment containing sacB gene was synthesized, and the synthesized DNA fragment and pUC19K vector were cut with XbaI and SpeI to ligate, thereby constructing pSacHR06 vector containing sacB gene (FIG. 1).

As the pSacHR06 vector has sacB gene origined from *Bacillus subtilus* and it can easily remove the origin of DNA replication using restriction enzyme and repeatedly ligate, it can be used in sacB positive selection.

```
SEQ ID NO: 1 (pucoriup):
5'-agccgtcgacgctagcgcatgcacgcgtgtgcacccatgggacg tcctcactgactcgctgcgctc-3'

SEQ ID NO: 2 (pucorido):
5'-ggctcacaacgtggctagcgacgtcgtgcacccatgggttccac tgagcgtcagacc-3'

SEQ ID NO: 3 (sacBf):
5'-actctctagacgcgggtttgttactgataa-3'

SEQ ID NO: 4 (sacBr):
5'-gctagatatcaggatatcggcattttcttt-3'
```

1-2: Disruption of lacI Gene in *E. coli* W3110 lacI gene encoding repressor of lac operon, which inhibits transcription of lac operon involved in lactose decomposition, was disrupted in *E. coli* W3110 (ATCC 39936) by one step inactivation method Datsenko et al., PNAS, 2000, Vol. 97, No. 12, pages 6640-6645) using primers set forth in SEQ ID NO:5 and SEQ ID NO:6 below, from which antibiotic resistance is removed, thus constructing *E. coli* W3110ΔlacI.

```
SEQ ID NO: 5 (lacI_1stup):
5'-gtgaaaccagtaacgttatacgatgtcgcagagtatgccggtg tctatagattgcagcattacacgtcttg-3'

SEQ ID NO: 6 (lacI_1stdo):
5'-tcactgcccgctttccagtcgggaaacctgtcgtgccagctgc attaatgcacttaacggctgacatggg-3'
```

1-3: Destruction of Feedback Inhibition of thrA

Feedback inhibition of thrA encoding aspartokinase I was disrupted by using homologous recombination vector pSacHR06 constructed in Example 1-1 and W3110ΔlacI constructed in Example 1-2, referring to the research results of Lee et al. (*J. Bacteriol.*, 185:5442, 2003).

Chromosomal DNA of *E. coli* W3110 (ATCC 39936) isolated and purified according to a method known in the art (Sambrook et al., Molecular cloning, 2$^{nd}$ ed, Cold Spring Harbor Laboratory Press, NY, 1989), as a template, was subjected to PCR using primers set forth in SEQ ID NO: 7 and SEQ ID NO: 8 below, and primers set forth in SEQ ID NO: 9 and SEQ ID NO: 10, and the obtained two PCR fragments were mixed at the same concentration, and then subjected to overlapping PCR as a template using primers set forth in SEQ ID NO: 7 and SEQ ID NO: 10 below. After 1279 bp PCR fragment obtained by the method was cut with restriction enzymes BamHI and SalI and inserted in pSacHR06 cut with restriction enzymes BamHI and SalI, the sequence was analyzed. As a result, it was confirmed that the 1034$^{th}$ base (C) of thrA was substituted with (T).

After the obtained vector was cut with NheI enzyme to disrupt the origin of DNA replication, self-ligated, and electrophorated into competent W3110ΔlacI cells, thus obtaining a strain having feedback inhibition of thrA disrupted, using sacB positive selection.

```
SEQ ID NO: 7 (thrA1):
5'-acgcggatccatcgccattatggccggcgtattagaagc-3'

SEQ ID NO: 8 (thrA2):
5'-gattgcgtaatcagcaccacgaaaatacgggcgcgtgacatcg-3'

SEQ ID NO: 9 (thrA3):
5'-cgatgtcacgcgcccgtattttcgtggtgctgattacgcaatc-3'

SEQ ID NO: 10 (thrA4):
5'-cacgcgtcgacctggaagtgcagttaacaatgaccggg-3'
```

1-4: Destruction of Feedback Inhibition of lysC

Referring to the research results (Ogawa-Myyata et al., *Biosci. Biotechnol. Biochem.*, 65:1149, 2001), feedback inhibition of lysC gene encoding aspartokinase III was disrupted in the strain having feedback inhibition of thrA disrupted, which is constructed in Example 1-3. After chromosomal DNA of *E. coli* W3110 (ATCC 39936), as a template, was subjected to PCR using primers set forth in SEQ ID NO: 11 and SEQ ID NO: 12 below, and primers set forth in SEQ ID NO: 13 and SEQ ID NO: 14, the obtained two PCR fragments were mixed at same concentration, and then subjected to overlapping PCR as a template using primers set forth in SEQ ID NO: 11 and SEQ ID NO: 14 below. 1484 bp PCR fragment, obtained by the above described method, was digested with restriction enzymes BamHI and SalI to insert in pSacHR06 digested with restriction enzymes BamHI and SalI, thus analyzing sequence thereof. As a result, it was confirmed that the 1055$^{th}$ base (C) of lysC was substituted with (T).

After the obtained vector was cut with NheI enzyme to disrupt the origin of DNA replication, self-ligated, and electrophorated into competent W3110ΔlacI cells having feedback inhibition of thrA disrupted, which is constructed in Example 1-3, thus obtaining a strain having feedback inhibition of lysC disrupted by sacB positive selection.

```
SEQ ID NO: 11 (lysC1):
5'-ctgatgtcgaccctgctgtttgttgagatcctgcgc-3'

SEQ ID NO: 12 (lysC2):
5'-ggttgaaccggtggtatcaaggataatgccacgctcacttctg-3'

SEQ ID NO: 13 (lysC3):
5'-cagaagtgagcgtggcattaatccttgataccaccggttcaacc-3'

SEQ ID NO: 14 (lysC4):
5'-ccagctaaatgacgcttcaggatccggtttataag-3'
```

1-5: Substitution of Promoter of L-Threonine Operon (thrABC)

In order to disrupt regulation of transcriptional expression by attenuation in *E. coli* W3110 having feedback inhibition of thrA gene and lysC gene disrupted, which is constructed in Example 1-4, a promoter of threonine operon containing an attenuator sequence was substituted with tac promoter which is a strong promoter.

For the substitution, after *E. coli* W3110 genomic DNA, as a template, was subjected to PCR using primers set forth in SEQ ID NO: 15 and SEQ ID NO: 16 below to obtain a 725 bp PCR fragment, the obtained PCR fragment was cut with PvuII and SphI, and cloned into the corresponding enzyme cutting site of pKK223-3 vector (Pharmacia Biotech, USA).

Meanwhile, after PCR was carried out using primers set forth in SEQ ID NO: 17 and SEQ ID NO: 18 below to obtain a 705 bp PCR fragment, cloning was performed by digesting the obtained fragment with EcoRI and PstI to ligate into pKK223-3 digested with the same enzymes. After base sequence of the vector was analyzed, a fragment cut with PvuII and PstI was ligated to pSacHR06 vector cut with the same enzyme to transform into *E. coli* W3110 having feedback inhibition of thrA gene and lysC gene disrupted, thus constructing *E. coli* having a promoter containing attenuator substituted with tac promoter.

```
SEQ ID NO: 15 (thrAT1):
5'-gcagccagctgtagcgatctgcggattgtcgatagt-3'

SEQ ID NO: 16 (thrAT2):
5'-caggagcatgccagaagctgctatcagacactcttt-3'

SEQ ID NO: 17 (thrAT3):
5'-cagcagaattcatgcgagtgttgaagttcggcggta-3'

SEQ ID NO: 18 (thrAT4):
5'-cagagctgcagtccgtccaaatctcgcaacaatcgg-3'
```

1-6: Disruption of lysA, metA, tdh and iclR genes lysA, metA, tdh and iclR genes were disrupted by one step inactivation method Datsenko et al., PNAS, 2000, Vol. 97, No. 12, pages 6640-6645), and an antibiotic resistance marker gene was removed in W3110, in which feedback inhibition of lacI gene obtained in Example 1-5, thrA and lysC is disrupted, and a promoter of thrABC operon is substituted with tac promoter.

In order to construct a strain having lysA gene encoding diaminopimelate decarboxylase disrupted, a PCR reaction was performed using primers set forth in SEQ ID NO:19 and SEQ ID NO:20 below and pKD4 plasmid Datsenko et al., PNAS, 2000, Vol. 97, No. 12, pages 6640-6645) to obtain DNA fragment, which was then electrophorated into competent W3110 cells in which feedback inhibition of lad gene containing pKD46 Datsenko et al., PNAS, 2000, Vol. 97, No. 12, pages 6640-6645, GenBank No. AY048746), and thrA and lysC are disrupted, and a promoter of thrABC operon was substituted with tac promoter. After this, kanamycin-resistant cell lines were subjected to PCR to confirm lysA gene disruption, into which pCP20 plasmid was introduced to remove an antibiotic resistance marker gene Datsenko et al., PNAS, 2000, Vol. 97, No. 12, pages 6640-6645).

```
SEQ ID NO: 19 (KOlysA1):
5'-atgccacattcactgttcagcaccgataccgatctcaccgccga aaatctgattgcagcattacacgtcttg-3'

SEQ ID NO: 20 (KOlysA2):
5'-gttgataaggaacagaaagcccaccgcccgcagaaatagcctgt aaatcccacttaacggctgacatggga-3'
```

In order to construct a strain having metA gene encoding homoserine O-succinyltransferse disrupted, metA gene was disrupted by one step inactivation using primers set forth in SEQ ID NO: 21 and SEQ ID NO: 22 below, and an antibiotic resistance marker gene was removed.

```
SEQ ID NO: 21 (KOmetA1):
5'-gtgtgccggacgagctacccgccgtcaatttcttgcgtgaag aaaacgtctttgtgattgcagcattacacgtcttg-3'

SEQ ID NO: 22 (KOmetA2):
5'-cgggatggcccgtcacaaaggcaatgcgcttatctttactgg caaacagacacttaacggctgacatggga-3'
```

In order to construct a strain having tdh gene encoding L-threonine dehydrogenase disrupted, tdh gene was disrupted by one step inactivation using primers set forth in SEQ ID NO: 23 and SEQ ID NO: 24 below, and an antibiotic resistance marker gene was removed.

```
SEQ ID NO: 23 (KOtdh1):
5'-atgaaagcgttatccaaactgaaagcggaagagggcatctggat gaccgagattgcagcattacacgtcttg-3'

SEQ ID NO: 24 (KOtdh2):
5'-atcactttggtccagtcgatagacatatcagacggcggaatacc cagcatcacttaacggctgacatggga-3'
```

In order to construct a strain having disrupted iclR gene encoding a regulatory protein inhibiting the expression of glyoxylate shunt, iclR gene was disrupted by one step inactivation using primers set forth in SEQ ID NO: 25 and SEQ ID NO: 26 below, and an antibiotic resistance marker gene was removed.

```
SEQ ID NO: 25 (KOiclR1):
5'-tgaaaatgataccacgatacagaaaaaagagactgtcatggtc gcacccgattgcagcattacacgtcttg-3'

SEQ ID NO: 26 (KOiclR2):
5'-atagaaattgcggcaaacggttcacggtgctcatcgaaaatac acgctgccacttaacggctgacatggga-3'
```

1-7: Construction of Microorganism Having a Weak Threonine Dehydratase Activity

In order to increase L-threonine production by decreasing the production of L-isoleucine produced using L-threonine as a substrate, a strain was constructed by generating site specific mutation in ilvA gene encoding threonine dehydratase which is the first enzyme of the corresponding pathway, referring to the research results of Lee et al. (Lee et al., *J. Bacteriol.*, 185:5442, 2003), thus confirming that the growth of the constructed strain was significantly influenced by the concentration of L-isoleucine added in a medium.

First, ilvA gene was disrupted by one step inactivation using a chromosomal DNA of *E. coli* W3110 (ATCC 39936) as a template with primers set forth in SEQ ID NO: 27 and SEQ ID NO: 28 below to select chloramphenicol-resistant cell lines, thus confirming that ilvA gene was disrupted using PCR.

Meanwhile, chromosomal DNA of *E. coli* W3110 (ATCC 39936), as a template, was subjected to PCR reactions using a primer pair set forth in SEQ ID NO: 29 and SEQ ID NO: 30 below, and a primer pair set forth in SEQ ID NO: 31 and SEQ ID NO: 32 below, respectively to obtain 648 bp and 676 bp DNA fragments, which were then mixed at same concentration to perform overlapping PCR using primers set forth in SEQ ID NO: 29 and SEQ ID NO: 32 below. After the 1287 bp PCR fragment obtained by PCR was cut with restriction enzymes BamHI and SalI to insert in pSacHR06 cut with restriction enzymes BamHI and SalI, thus analyzing sequence thereof. As a result, it was confirmed that the 290$^{th}$ base (C) of ilvA was substituted with (T). The obtained vector was cut with NheI enzyme to disrupt the origin of DNA replication, self-ligated, and electrophorated into competent cells of the mutant microorganism constructed in Example 1-6. And then, the strain was selected by sacB positive selection (Wohlleben et al., *J. Bacteriol.*, 174:5462, 1992) and chloramphenicol sensitivity, thus obtaining a strain having a weak threonine dehydratase activity.

```
SEQ ID NO: 27 (KOilvA1):
5'-atcgccagccagtgcacagctttaagctgcgcggcgcatacgc catgatggattgcagcattacacgtcttg-3'

SEQ ID NO: 28 (KOilvA2):
5'-cccctgctgctgtgacagttcgatcgctttggctttcgcttca tcaaagtcacttaacggctgacatggga-3'

SEQ ID NO: 29 (ilvA1):
5'-gacgggatccgcaaagcctgtgcgctgatcaccgacgg-3'

SEQ ID NO: 30 (ilvA2):
5'-cacgcctaaccgcgcagaaaaaaacgcgacgccctgcg-3'

SEQ ID NO: 31 (ilvA3):
5'-cgcagggcgtcgcgtattactgcgcggttaggcgtg-3'

SEQ ID NO: 32 (ilvA4):
5'-caggtactgcagaccggaaagaatatgcgccagccgttcg-3'
```

1-8: Construction of Plasmid pMloxC

In case of disrupting genes using one step inactivation, one FRT or loxP sequence, which is a recombinase recognition site, is left behind in chromosomal DNA, every time one gene is disrupted. As a result, it is difficult to construct mutant microorganisms because non-targeted sites are disrupted upon continuous disruption of large amounts of genes (Nagy A., *Genesis*, 26:99, 2000). Suzuki et al., disclosed an improved method for disrupting genes using mutant loxP named lox71 and lox66 to solve the above described problem (*Appl. Environ. Microbiol.*, 71:8472, 2005). Accordingly, the present inventors constructed a new vector pMloxC into which lox71 and lox66 were introduced (*Nucleic Acids Res.*, 24:2519, 1996) in order to make the method to be used more easily.

Figure 2:
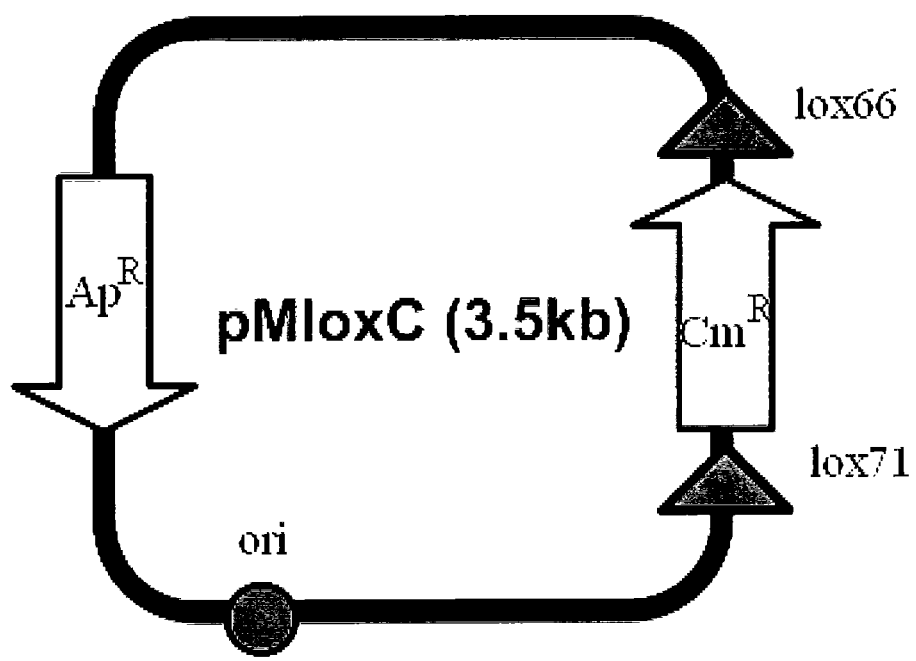
FIG. 2 is a cleavage map of recombinant vector pMloxC containing lox66, lox71 and a chloramphenicol resistance marker gene.

In order to construct the vector, pUG6 plasmid (*New England Biolab.*, USA) was cut with HindIII and EcoRV to obtain a 2,427 bp DNA fragment, and Pacyc184 plasmid (*New England Biolab.*, USA), as a template, was subjected to PCR using primers set forth in SEQ ID NO:33 and SEQ ID NO:34 below to obtain a 1,100 bp PCR fragment. The obtained fragments were cut with EcoRV/HindIII and HindIII/SmaI to ligate, thereby constructing pMloxC (FIG. 2).

```
SEQ ID NO: 33 (ECmulox_up):
5'-atataagctt taccgttcgtatagcatacattatacgaagtta tctgccctgaaccgacgaccg-3'

SEQ ID NO: 34 (ECmulox_do):
5'-aattcccggg accgttcgtataatgtatgctatacgaagttat gcatcacccgacgcactttgc-3'
```

1-9: Disruption of tdcC Gene

In order to construct a strain having tdcC gene encoding threonine/serine transporter disrupted, pMloxC vector constructed in Example 1-8, as a template, was subjected to PCR using primers set forth in SEQ ID NO:35 and SEQ ID NO:36 below, and then the resulting DNA fragment was isolated and purified. The purified DNA fragment, as a template, was subjected to PCR using primers set forth in SEQ ID NO:37 and SEQ ID NO:38 below.

Using the obtained DNA fragment, tdcC gene was disrupted by the one step inactivation and an antibiotic resistance marker gene was removed.

```
SEQ ID NO: 35 (KOtdcC1):
5'-gcgtaaatcagataccacatggacgttaggcttgtttggtacggc aatcgtaggtgacactatagaacgcg-3'

SEQ ID NO: 36 (KOtdcC3):
5'-ccagtgtaatcgcgaacgttgttttggtaccggtcatggacgcaa agtggtagtggatctgatgggtacc-3'

SEQ ID NO: 37 (KOtdcC2):
5'-atgagtacttcagatagcattgtatccagccagacaaaacaatcg tcctggcgtaaatcagataccacat-3'

SEQ ID NO: 38 (KOtdcC4):
5'-gaagaaagatttgaagatagccacgagtgcgatgatggaagccgc atattccagtgtaatcgcgaacgt-3'
```

1-10: Substitution of Promoter of ppc Gene

A promoter of ppc gene encoding phosphoenolpyruvate carboxylase on chromosome was substituted with a strong promoter, thus constructing a strain having increased enzyme activity. In order to substitute a promoter of ppc gene, the constructed pMloxC plasmid was subjected to PCR as a template using primers set forth in SEQ ID NO: 39 and SEQ ID NO: 40 below, and then, the resulting DNA fragment, as a template, was subjected to PCR using primers set forth in SEQ ID NO: 41 and SEQ ID NO: 42 below. After that, the resulting DNA fragment, as a template, was subjected to PCR using primers set forth in SEQ ID NO: 43 and SEQ ID NO: 44 below. The finally obtained DNA fragment was inserted in ppc gene using the same method as the above one step inactivation, and an antibiotic resistance marker gene was removed therefrom, thereby constructing a strain having a stronger trc promoter than a native promoter of ppc by substitution.

```
SEQ ID NO: 39 (FPppc1):
5'-ctgcgggcaaccatgcgcaaggggtttccctctcctgcgcgat gctgggttaggtgacactatagaacgcg-3'
```

-continued

```
SEQ ID NO: 40 (RPppc1):
5'-tctgcgctttggcttccgccatgttggccggagacagagtaaa caggcagctaaaggcaaagaac-3'

SEQ ID NO: 41 (FPppc2):
5'-attaagttcactgaccgatgcggaaaaacgcaaaggcgtggtg gcctgttctgcgggcaaccatgcgcaa-3'

SEQ ID NO: 42 (RPppc2):
5'-ctgcgggcaaccatgcgcaaggggtttccctctcctgcgcgat gctgggttaggtgacactatagaacgcg-3'

SEQ ID NO: 43 (FPppc3):
5'-ggcagctaaaggcaaagaacatcaccactgcaaccatcagcat gcttagtggatctgatgggtacc-3'

SEQ ID NO: 44 (RPppc3):
5'-attaagttcactgaccgatgcggaaaaacgcaaaggcgtgtgg cctgttctgcgggcaaccatgcgcaa-3'
```

1-11: Substitution of Promoter of acs Gene

In order to reduce the amount of acetic acid produced during Fed-batch culture of threonine-producing microorganisms, a strain having increased enzyme activity was constructed by substituting a promoter of acs gene encoding acetyl CoA synthetase on chromosome with a strong promoter. To substitute a promoter of acs, the constructed pMloxC plasmid, as a template, was subjected to PCR using primers set forth in SEQ ID NO: 45 and SEQ ID NO: 46 below, and then, the obtained DNA fragment, as a template, was subjected to PCR using primers set forth in SEQ ID NO: 47 and SEQ ID NO: 48 below. After that, the DNA fragment obtained by PCR was subjected to PCR as a template using primers set forth in SEQ ID NO: 49 and SEQ ID NO: 50 below, and the finally obtained DNA fragment was inserted in acs gene by the same method as the above described one step inactivation, and then an antibiotic resistance marker gene was removed therefrom, thereby constructing a strain having a stronger trc promoter than the promoter of acs by substitution.

```
SEQ ID NO: 45 (FPacs1):
5'-gccctatgtgtaacaaataaccacactgtgaatgttgtctaggt gacactatagaacgcg-3'

SEQ ID NO: 46 (RPacs1):
5'-tgttatccgctcacaattccacacattatacgagccggatgatta attgtcaacagctagtggatctgatgggtacc-3'

SEQ ID NO: 47 (FPacs2):
5'-tcacgacagtaaccgcacctacactgtcatgacattgctcgcccc tatgtgtaacaaata-3'

SEQ ID NO: 48 (RPacs2):
5'-cgatgaggcaggaatggtgtgtttgtgaatttggctcatggtctg tttcctgtgtgaaattgttatccgctcacaattcc-3'

SEQ ID NO: 49 (FPacs3):
5'-cgaattgcgccattgttgcaatggcggtttttattgtttttcacg acagtaaccgcacct-3'
```

```
SEQ ID NO: 50 (RPacs3):
5'-ttgttgatacatcgcctcgtactgctgagggtttatcaggcaacg gtctgcgatgttggcaggaatggtg-3'
```

1-12: Construction of pBRThrE Vector (1) Construction of pKKThrABC Vector

To clone a vector containing operon (thrABC) involved in L-threonine biosynthesis, which is the most important gene in L-threonine biosynthesis, chromosomal DNA of a mutant microorganism having thrA gene released from the feedback inhibition, which is constructed in Example 1-3 was subjected to PCR as a template using primers set forth in SEQ ID NO: 51 and SEQ ID NO: 52 below. The resulting synthesized DNA fragment was cut with XmaI and HindIII, and cloned into pKK223-3 vector (Pharmacia Biotech., USA) cut with the same restriction enzyme, and then its sequence was analyzed, thereby constructing pKKThrABC vector containing 9.4 kb operon (thrABC) involved in L-theronine biosynthesis.

```
SEQ ID NO: 51 (Thr_Xma):
5'-gttgcccgggatgcgagtgttgaagttcgg-3'

SEQ ID NO: 52 (Thr_Hin):
5'-gcgtcaagcttcggcggttgttattctccgc-3'
```

(2) Construction of pBRThrABC Vector

Figure 3:
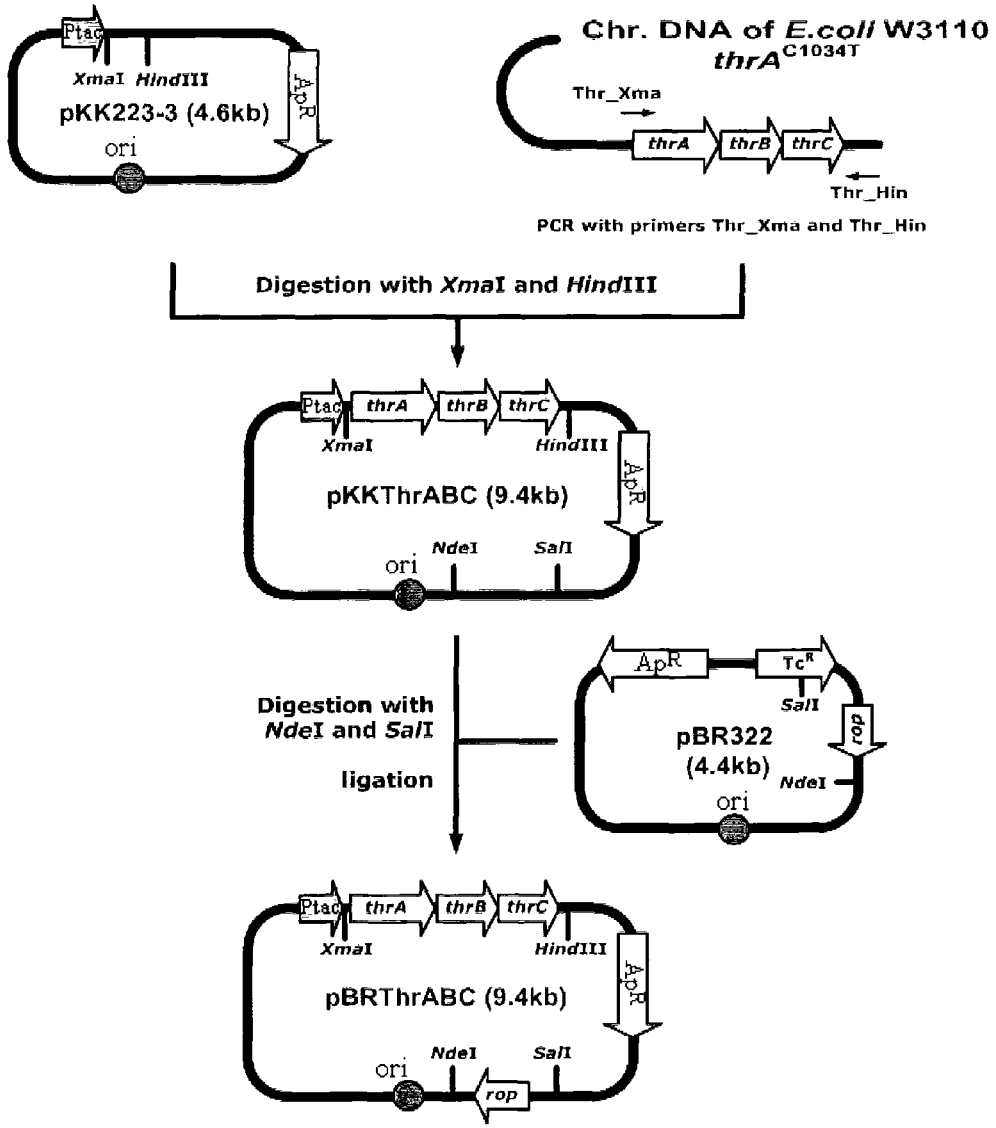
FIG. 3 shows a process for constructing recombinant vector pBRThrABC containing thrABC operon.

In order to increase the stability of the above constructed pKKThrABC vector, pBR322 vector (New England Biolab., USA) was cut with NdeI and SalI to obtain 1.6 kb DNA fragment containing rop gene, and pKKThrABC vector constructed in Example 1-12(1) was cut with the same restriction enzymes to obtain 7.8 kb DNA fragment, followed by ligating the obtained fragments, thereby constructing 9.4 kb pBRThrABC vector (FIG. 3).

(3) Construction of pBRthrR Vector

Figure 4:
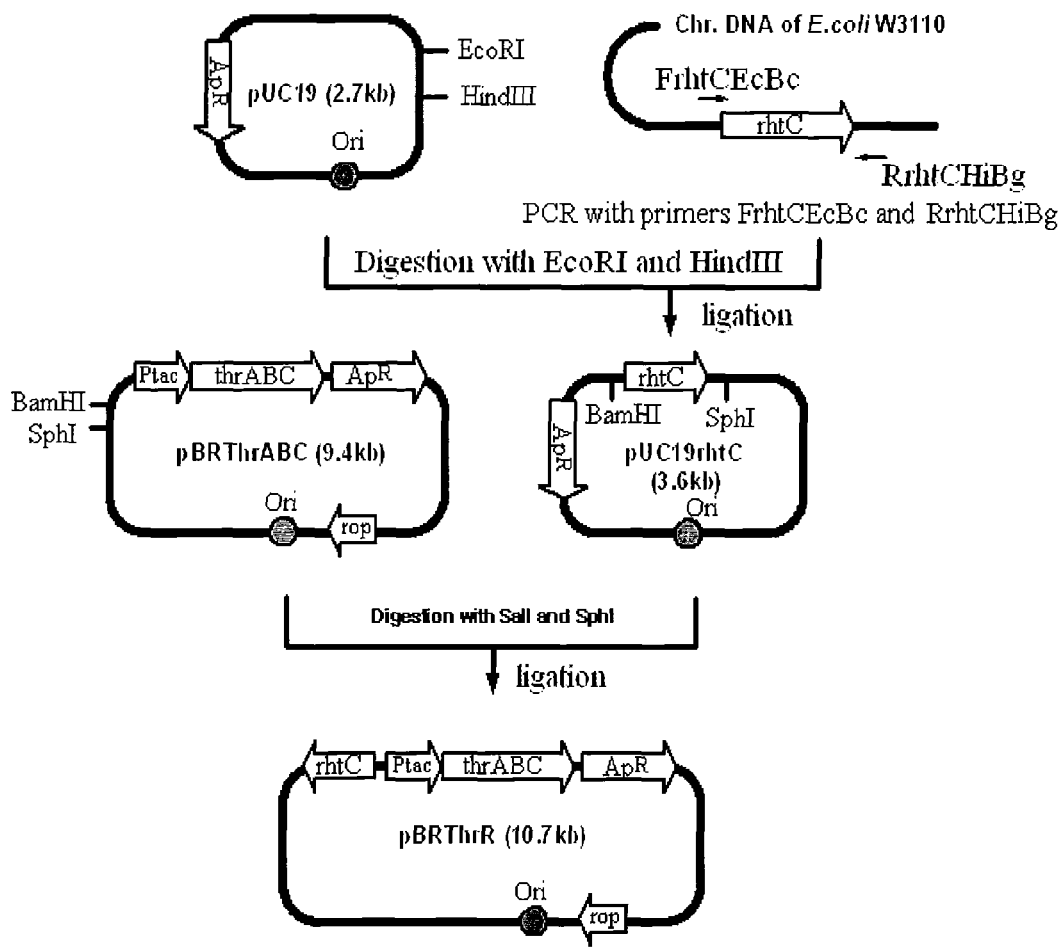
FIG. 4 shows a process for constructing recombinant vector pBRThrR containing thrABC operon and rhtC.

In order to introduce rhtC encoding threonine exporter into the constructed pBRThrABC vector, chromosomal DNA of E. coli W3110, as a template, was subjected to PCR using primers set forth in SEQ ID NO: 53 and SEQ ID NO: 54 below, and the obtained DNA fragment was cut with EcoRI and Hind III and cloned into pUC19 vector cut with the same restriction enzymes, and then its sequence was synthesized, thereby constructing pUC19rhtC vector. Finally, pBRThrABC vector constructed in Example 1-12(2) and pUC19rhtC vector were simultaneously cut with BamHI and SphI to clone, thus constructing 10.7 kb pBRThrR vector (FIG. 4).

```
SEQ ID NO: 53 (FrhtCEcBa):
5'-ctgagaattcggatccagatggctgaacagatgc-3'

SEQ ID NO: 54 (RrhtCHiBg):
5'-cctacaagcttagatctcaaagcagatgaaggcgc-3'
```

(4) Construction of pBRthrR2 Vector

In order to introduce rhtA known as threonine and homoserine exporter into the pBRThrR vector, first, chromosomal DNA of E. coli W3110, as a template, was subjected to PCR using primers set forth in SEQ ID NO: 55 and SEQ ID NO: 56 below, and the obtained DNA fragment was cut with MluI and SalI and cloned into pBRThrR vector constructed in Example 1-12(3), which was cut with the same restriction enzymes, and then its sequence was analyzed, thereby constructing pBRThrR2 vector having 11.1 kb rhtA introduced thereto.

```
SEQ ID NO: 55 (FrhtAMlu):
5'-ctgaacgcgtgaactgcgtaagtattacg-3'

SEQ ID NO: 56 (FrhtASalPst):
5'-ctgacgtcgacctgcagaccatgcagaaatgtaaat-3'
```

(5) Construction of pBRthrE Vector

Figure 5:
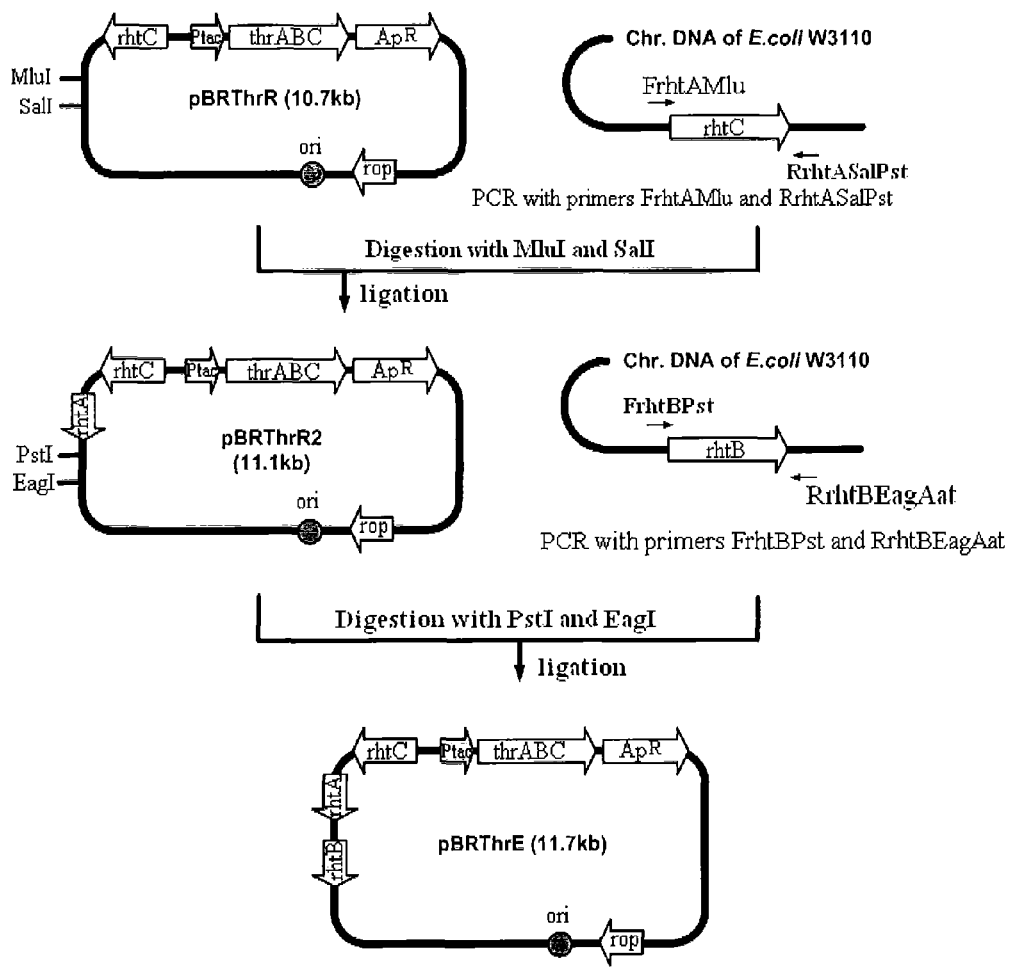
FIG. 5 shows a process for constructing recombinant vector pBRThrE containing thrABC operon, and rhtC, rhtB and rhtA.

In order to introduce rhtB assumed to be homoserine and homoserine lactone exporter, into the above constructed pBRThrR2 vector, first, chromosomal DNA of *E. coli* W3110, as a template, was subjected to PCR using primers set forth in SEQ ID NO: 57 and SEQ ID NO: 58 below, and the obtained DNA fragment was cut with PstI and EagI and cloned into pBRThrR2 vector cut with the same restriction enzymes and then its sequence was analyzed, thereby constructing pBRThrE vector having 11.7 kb rhtB introduced thereinto (FIG. 5).

```
SEQ ID NO: 57 (FrhtBPst):
5'-cgtagctgcagtccacaccagtaaactctg-3'

SEQ ID NO: 58 (FrhtBEagAat):
5'-catttcggccggacgtcagtcggataaggcgtttac-3'
```

1-13: Construction of L-Threonine-Producing Microorganism pBRthrR plasmid constructed in Example 1-12 was transduced into *E. coli* TH08 in which feedback inhibition of thrA and lysC was disrupted, a promoter of threnine operon was substituted with tac promoter, and lad, metA, lysA and tdh gene were disrupted through the process of Example 1-1 to Example 1-11, thereby constructing THR08 strain. After this, pBRThrR and pBRThrE vector constructed in Example 1-12 were respectively introduced into *E. coli* TH27 constructed by substituting ppc promoter of TH08 with trc promoter and disrupting iclR gene and tdcC gene therein, thereby constructing L-threonine-producing microorganisms, THR27 and THE27.

Figure 6:
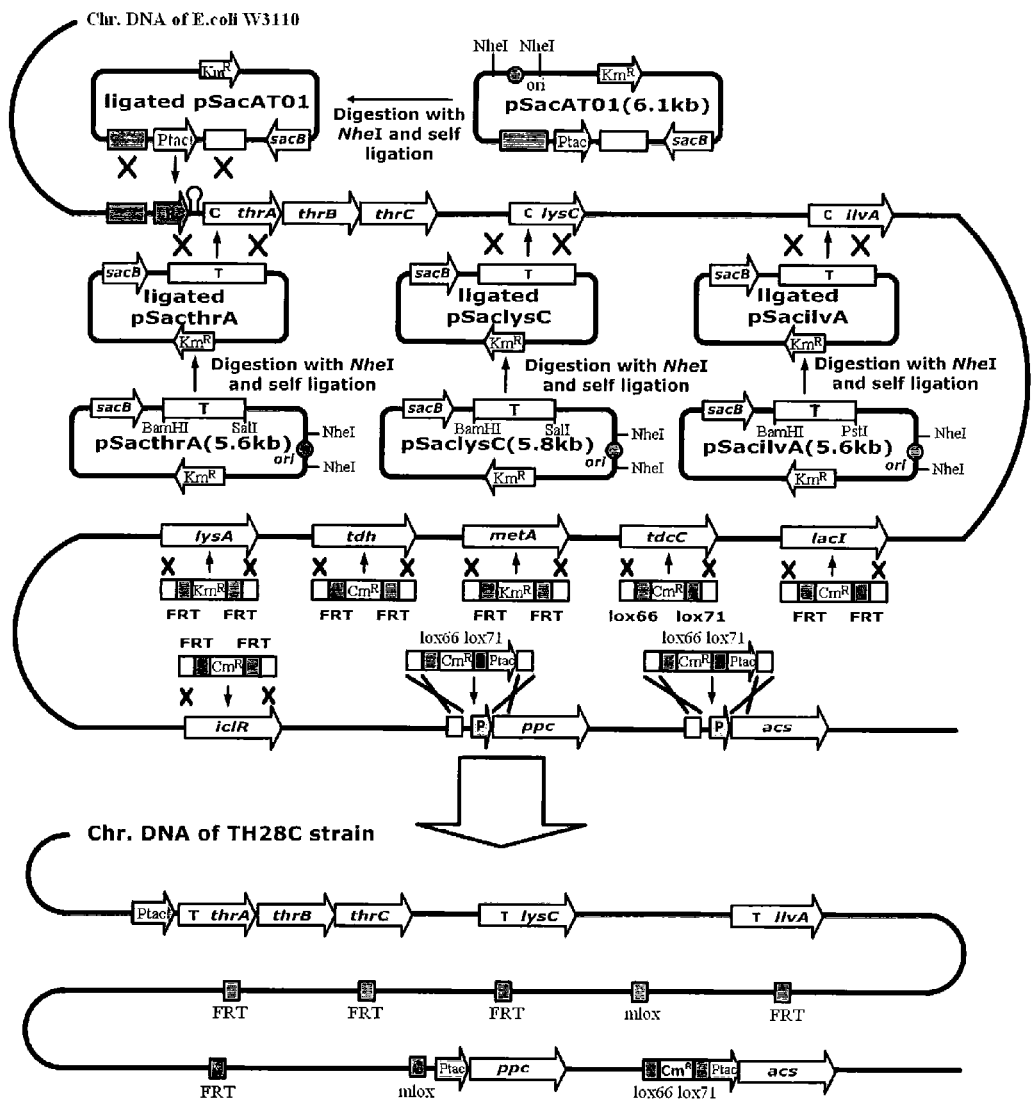
FIG. 6 shows a process for constructing a microorganism producing L-threonine according to the present invention by manipulating only a target gene from wild type E. coli W3110.

The pBRThrE vector was introduced into *E. coli* TH28 constructed by substituting a promoter of acs gene of the TH27 with trc promoter, thereby constructing L-threonine-producing microorganism THE28 (Table 1 and FIG. 6).

TABLE 1

Theonine-producing mutant strains according to the present invention

| Strains | Mutation |
|---|---|
| W3110 (parent strain) | wild type |
| TH08 | Disruption of feedback inhibition of thrA and lysC, substitution of promoter of thrABC, decrease in ilvA activity, ΔlacI, ΔmetA, ΔlysA, and Δtdh |
| TH27 | Disruption of feedback inhibition of thrA and lysC, substitution of promoter of thrABC, decrease in ilvA activity, ΔlacI, ΔmetA, ΔlysA, Δtdh, ΔiclR, ΔtdcC, substitution of promoter of ppc |
| TH28 | Disruption of feedback inhibition of thrA and lysC, substitution of promoter of thrABC, decrease in ilvA activity, ΔlacI, ΔmetA, ΔlysA, Δtdh, ΔiclR, ΔtdcC, substitution of promoter of ppc and acs |
| THR08 | TH08 + pBRThrR(thrABC + rhtC) |
| THR27 | TH27 + pBRThrR(thrABC + rhtC) |
| THE27 | TH27 + pBRThrE(thrABC + rhtC + rhtA + rhtB) |
| THE28 | TH28 + pBRThrE(thrABC + rhtC + rhtA + rhtB) |

Example 2

Preparation of L-Threonine Using L-Threonine-Producing Microorganism

In order to examine L-threonine-producing ability of THR08 constructed in Example 1, the L-threonine-producing ability of parent strain *E. coli* W3110 and that of THR08 microorganism were compared under the same conditions. The two strains were subcultured in LB medium added with 50 μg/ml of ampicillin to inoculate in a titration medium shown in Table 2, and then cultured at 31° C. and 250 rpm for 48 min, thus measuring the concentration of L-threonine in culture broth by HPLC.

As a result, it was confirmed that 17.8~18.4 g/l of L-threonine, which was not produced in W3110 wild type, was produced in THR08 strain, as shown in Table 3.

TABLE 2

Composition of L-threonine titer medium

| Components | Concentration (per liter) |
|---|---|
| glucose | 50 g |
| $KH_2PO_4$ | 4 g |
| $(NH_4)_2SO_4 \cdot 7H_2O$ | 14 g |
| $MnSO_4 \cdot 5H_2O$ | 10 mg |
| $FeSO_4 \cdot 7H_2O$ | 5 mg |
| $MgSO_4 \cdot 7H_2O$ | 2 g |
| L-methionine | 150 mg |
| L-lysine | 150 mg |
| yeast extract | 2 g |
| trace metal solution | 5 ml |
| betaine | 1 g |
| $CaCO_3$ | 30 g |

* trace metal solution (containing 10 g $FeSO_4 \cdot 7H_2O$, 1.35 g $CaCl_2$, 2.25 g $ZnSO_4 \cdot 7H_2O$, 0.5 g $MnSO_4 \cdot 4H_2O$, 1 g $CuSO_4 \cdot 5H_2O$, 0.106 g $(NH_4)_6Mo_7O_{24} \cdot 4H_2O$, 0.23 g $Na_2B_4O_7 \cdot 10H_2O$, 10 ml of 35% HCl per 1 L distilled water)

TABLE 3

The amount of L-threonine produced according to each strain

| | Microorganism | |
|---|---|---|
| | W3110 | THR08 |
| L-threonine (g/l) | 0 | 17.8~18.4 |

Example 3

Preparation of L-Threonine Using L-Threonine-Producing Microorganisms THR27 and THE27

In order to examine L-threonine productivity of THR27 and THE27 constructed in Example 1, they were selected on LB plate containing 50 g/ml ampicillin. Each of 1% of the selected microorganisms were inoculated into four 500 ml Sakaguchi flasks having 50 ml of LB medium supplemented with 5 g/l of glucose, 0.15 g/l of L-methionine, 0.22 g/l of L-lysin and shake-cultured 250 times per minute through a horizontal movement at 31° C. for 12 hours, thus obtaining precultured broth. In order to produce L-threonine, 1.8 L of production medium having the composition shown in Table 4 was put into 5 L of small-sized fermenter, and 200 ml of the obtained prebcultured broth was inoculated in a fermenter to culture at 31° C., while automatically controlling the stirring speed to maintain 40% of oxygen partial pressure ratio, until the concentration of glucose added in the medium reached 0 g/l.

At this time, the pH level of the culture was maintained at 6.0~6.5 by using ammonia water. Table 5 shows the amount of L-threonine accumulated in fermented broth after completion of fermentation. As shown in Table 5, it was observed that L-threonine productivity of parent strain THR08 was 9.2 g/l, whereas L-threonine productivity of the microorganisms constructed therefrom was 11.2~11.9 g/l, which is higher than that of the parent strain. Based on the results it was suggested that the concentration of L-threonine was increased by about 21.7~29.4%, compared to the parent strain.

TABLE 4 production medium of L-threonine

| Components | Concentration (per liter) |
|---|---|
| glucose | 30 g |
| $KH_2PO_4$ | 2 g |
| $(NH_4)_2SO_4 \cdot 7H_2O$ | 10 g |
| $MnSO_4 \cdot 5H_2O$ | 5 mg |
| $MgSO_4 \cdot 7H_2O$ | 2 g |
| L-methionine | 300 mg |
| L-lysine | 440 mg |
| L-isoleucine | 100 mg |
| trace metal solution | 10 ml |
| yeast extract | 2 g |
| biotin | 0.1 mg |
| thiamine | 0.1 g |
| betaine | 1 g |

* trace metal solution (containing 10 g $FeSO_4 \cdot 7H_2O$, 1.35 g $CaCl_2$, 2.25 g $ZnSO_4 \cdot 7H_2O$, 0.5 g $MnSO_4 \cdot 4H_2O$, 1 g $CuSO_4 \cdot 5H_2O$, 0.106 g $(NH_4)_6Mo_7O_{24} \cdot 4H_2O$, 0.23 g $Na_2B_4O_7 \cdot 10H_2O$, 10 ml of 35% HCl per 1 L distilled water)

TABLE 5

Productivity of L-threonine

| Strains | L-threonine (g/l) | acetate (g/l) | Culture time (hours) | $OD_{600}$ | Yield (%) |
|---|---|---|---|---|---|
| THR08 | 9.2 | 0.8 | 15.9 | 23.0 | 31 |
| THR27 | 11.2 | 0.6 | 14.1 | 20.2 | 37 |
| THE27 | 11.8 | 0.6 | 15.3 | 21.2 | 39 |

Example 4

Preparation of L-Threonine Using Fed-Batch Fermentation of L-Threonine-Producing Microorganisms THE27 and THE28

In order to examine L-threonine productivity of THE27 and THE28 constructed in Example 1 using fed-batch culture, they were selected on LB medium added with 50 µg/ml of ampicillin. Each of 1% of the selected microorganisms were inoculated into four 500 ml Sakaguchi flasks having 50 ml of LB medium supplemented with 5 g/l of glucose, 0.15 g/l of L-methionine, 0.22 g/l of L-lysin and shake-cultured 250 times per minute through a horizontal movement at 31° C. for 12 hours, thus obtaining precultured broth. In order to produce L-threonine, 1.8 L of production medium having the composition shown in Table 4 was put into 5 L of small-sized fermenter, and 200 ml of the obtained prebcultured broth was inoculated in a fermenter to culture at 31° C., while automatically controlling the stirring speed to maintain 40% of oxygen partial pressure ratio. At this time, when the concentration of glucose added in the medium decreased to less than 1 g/l, threonine-containing medium (Table 6) was replaced up to 14 times, and the pH level of the culture was maintained at 6.0-6.5 by using ammonia water.

Table 7 shows the amount of L-threonine accumulated in fermented broth after the completion of fermentation. As shown in Table 7, it was observed that L-threonine productivity of THE27 was 77.1 g/l, whereas L-threonine productivity of THE28 constructed from THE27 was 82.4 g/l, which is higher than that of the parent strain. In case of acetate, a main byproduct, it was observed that THE27 strain produced 7.85 g/L, whereas THE28 strain produced 2.35 g/L, showing a 70% decrease compared to the parent strain, as a result, culture time was also shortened by 10.9% from 56.1 hours to 50 hours, thus resulting in a 20.4% increase in L-threonine productivity.

TABLE 6

L-threonine-containing medium

| Compositions | Addition amount (g/80 ml) |
|---|---|
| glucose | 40 |
| $KH_2PO_4$ | 1 |
| L-methionine | 0.24 |
| L-lysine | 0.35 |

TABLE 7

Production amount of L-threonine

| Strains | L-threonine (g/l) | Acetate (g/l) | Culture time (h) | $OD_{600}$ |
|---|---|---|---|---|
| THE27 | 77.1 | 7.85 | 56.1 | 74.2 |
| THE28 | 82.4 | 2.35 | 50.0 | 82.6 |

INDUSTRIAL APPLICABILITY

As described and proven above in detail, the present invention provides a mutant microorganism overproducing L-threonine prepared by only site-specific mutation and a method for preparing L-threonine using the mutant microorganism. By using the mutant microorganism according to the present invention, L-threonine can be prepared at high yield, additional strain development becomes possible and their physiological phenomena can be easily understood since genetic information of L-threonine producing microorganism can be identified.

Although a specific embodiment of the present invention has been described in detail, those skilled in the art will appreciate that this description is merely a preferred embodiment and is not construed to limit the scope of the present invention. Thus, the substantial scope of the present invention will be defined by the accompanying claims and equivalents thereof.

What is claimed is:

1. A method for preparing *Escherichia coli* (*E. coli*) producing L-threonine, using site-specific mutation, the method comprising:
    (a) disrupting lacI, metA, lysA and tdh in the *E. coli*;
    (b) mutating ilvA, thrA and lysC in the *E. coli*;
    (c) inducing substitution of a promoter of L-threonine operon or acetyl CoA synthetase with a promoter selected from the group consisting of trc promoter, tac promoter, T7 promoter, lac promoter and trp promoter in the *E. coli*; and
    (d) introducing a vector containing one or more genes selected from the group consisting of a gene encoding L-threonine operon, rhtC, rhtA and rhtB into the *E. coli*.

2. The method according to claim 1 further comprising disrupting iclR and tdcC in the *E. coli*.

3. The method according to claim 1 further comprising substituting a promoter of a gene encoding phosphoenolpyruvate carboxylase with a promoter selected from the group consisting of trc promoter, tac promoter, T7 promoter, lac promoter and trp promoter in the *E. coli*.

* * * * *